(12) United States Patent
Smiley et al.

(10) Patent No.: US 7,919,683 B2
(45) Date of Patent: Apr. 5, 2011

(54) **CLONING AND SEQUENCING OF THE FERULATE ESTERASE GENE FROM *LACTOBACILLUS BUCHNERI* LN4017**

(75) Inventors: Brenda K. Smiley, Granger, IA (US); Annette Spielbauer, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 670 days.

(21) Appl. No.: 11/939,343

(22) Filed: Nov. 13, 2007

(65) Prior Publication Data

US 2008/0115241 A1 May 15, 2008

Related U.S. Application Data

(60) Provisional application No. 60/865,492, filed on Nov. 13, 2006.

(51) Int. Cl.
| | | |
|---|---|---|
| *C12N 15/31* | (2006.01) | |
| *C12N 15/52* | (2006.01) | |
| *C12N 15/63* | (2006.01) | |
| *C12N 15/82* | (2006.01) | |
| *A01H 5/00* | (2006.01) | |
| *C07H 21/04* | (2006.01) | |

(52) U.S. Cl. ........ 800/288; 800/287; 800/284; 800/278; 435/320.1; 435/440; 435/468; 536/23.7; 536/23.1; 536/23.2

(58) Field of Classification Search ........................ None
See application file for complete search history.

(56) References Cited

U.S. PATENT DOCUMENTS

| | | |
|---|---|---|
| 4,842,871 A | 6/1989 | Hill |
| 4,981,705 A | 1/1991 | Tomes |
| 5,747,020 A | 5/1998 | Rutherford et al. |
| 6,143,543 A | 11/2000 | Michelsen et al. |
| 6,326,037 B1 | 12/2001 | Mann et al. |
| 6,337,068 B1 | 1/2002 | Hendrick et al. |
| 6,403,084 B1 | 6/2002 | Chan et al. |
| 6,699,514 B2 | 3/2004 | Mann |
| 6,750,051 B2 | 6/2004 | Tricarico et al. |
| 2003/0024009 A1 | 1/2003 | Dunn-Coleman et al. |
| 2006/0005270 A1 | 1/2006 | Dunn-Coleman et al. |

FOREIGN PATENT DOCUMENTS

| | | |
|---|---|---|
| EP | 0 880 323 | 6/2001 |
| WO | WO 92/10945 | 7/1992 |
| WO | WO 93/13786 | 7/1993 |
| WO | WO 96/17525 | 6/1996 |
| WO | WO 02/068666 | 9/2002 |
| WO | WO 03/043411 | 5/2003 |
| WO | WO 2006/026763 | 3/2006 |
| WO | WO 2006/037334 | 4/2006 |

OTHER PUBLICATIONS

Donaghy, et al., Detection of ferulic acid esterase production by *Bacillus* spp. and lactobacilli, Appl. Microbiol. Biotech., (1998), 50:257-260.

Faulds, et al., Purification and characterization of a ferulic acid esterase (FAE-III) from *Aspergillus niger*: specificity for the phenolic moiety and binding to microcrystalline cellulose, Microbiology, (1994), 140:779-787.

Wang, et al., Purification and Characterization of a Feruloyl Esterase from the Intestinal Bacterium *Lactobacillus acidophilus*, Applied Environmental Microbiology, (2004), 70(4): 2367-2372.

Schrag, et al., Lipases and α/β Hydrolase Fold, Methods in Enzymology, (1997), 284: 85-107.

Tabka, et al., Enzymatic saccharification of wheat straw for bioethanol production by a combined cellulose xylanase and feruloyl esterase treatment, Enzyme and Microbial Technology, (2006), 39: 897-902.

Noelling, et al., Genome sequence and comparative analysis of the solven bacterium *Clostridium acetobutylicum*, Database UniProt [Online], (2001), XP002481439.

Luethi, et al., Cloning, Sequence Analysis, and Expression of Genes Encoding Xylan-Degrading Enzymes from the Thermophole. Caldocellum Saccharolyticum, Database UniProt[Online], (1991), XP002481440.

Luethi, et al., C. saccharolyticum xylanase A (XynA), beta-xylosidase (XynB) and acetyl esterase (XynC) genes, complete cds., Database EMBL [Online] (1990), XP002481441.

*Primary Examiner* — Brent Page
(74) *Attorney, Agent, or Firm* — Pioneer Hi-Bred International, Inc.; Kathryn K. Lappegard

(57) ABSTRACT

Embodiments of the present invention include polypeptides having ferulate esterase activity and the nucleic acid sequences that encode them. Methods of the embodiments utilize these ferulate esterase polypeptides and nucleic acid sequences to enhance the digestibility of plant cell walls and the accessibility of carbohydrates in plants. The invention provides for transgenic plants transformed with expression vectors containing a DNA sequence encoding ferulate esterase from *Lactobacillus buchneri*. Methods of using same to enhance plant fiber digestion in animals, are disclosed. Uses of this invention include, but are not limited to, forage and silage with improved digestibility for livestock, and enhanced biomass conversion.

35 Claims, 5 Drawing Sheets

SEQUENCE LISTING

```
<160> NUMBER OF SEQ ID NOS: 7

<210> SEQ ID NO 1
<211> LENGTH: 2508
<212> TYPE: DNA
<213> ORGANISM: Lactobacillus buchneri
<220> FEATURE:
<221> NAME/KEY: misc_feature
<222> LOCATION: (1)...(6)
<223> OTHER INFORMATION: HindIII restriction enzyme site
<221> NAME/KEY: misc_feature
<222> LOCATION: (1392)...(1397)
<223> OTHER INFORMATION: EcoRI restriction enzyme site
<221> NAME/KEY: CDS
<222> LOCATION: (540)...(1322)
<223> OTHER INFORMATION: Open Reading Frame of EST1
<221> NAME/KEY: CDS
<222> LOCATION: (1374)...(2174)
<223> OTHER INFORMATION: Open Reading Frame of EST2

<400> SEQUENCE: 1
aagctttaag ctccattgcc aacggggtta actctgctgc catggtgatc ggcatgatct      60
ccgttgcctt ctttgccaag aaattcaaga tcaagcggat cgtgatcgta gggttagtga     120
tcgcagctgt gggtcaatta ttggtattgt tctcagcatc tgtacattca gcagcacttt     180
catttattgg tgtcggaatt ggttctgccg gtttaggtgg tgctcaaagt ttagtttatg     240
tcttgttagc tgaaacggtt gatgaagggg aatatatctc tggtgtccgt gctcaaggct     300
tcttaacttc tatgggtact accggtgcta accttggtgc tggtttagca ggtgtcttag     360
tttccgctat cttggcacaa ttccactttg ttcctaacgt tgcccaatct gcttctggtt     420
taatggggat taacgtttgc ttcatttggt taccaattgc gatttatgta gtctgcatta     480
tcttagtttc gatgtatcgg acgacctatg acaaacaagt agtaaaggga gaataaacg      539 atg atc aaa ttt gta act act gaa atc aat gga tta acg ctt aga ggc      587
Met Ile Lys Phe Val Thr Thr Glu Ile Asn Gly Leu Thr Leu Arg Gly
  1               5                  10                  15 aca gct cat gtt cca gat ggt gaa cca gga cag cag ttt cca acg gtc      635
Thr Ala His Val Pro Asp Gly Glu Pro Gly Gln Gln Phe Pro Thr Val
```

```
                      20                     25                      30
tta atg ttt cat gga ttt gga gct gtt agg gat gaa ggc ttc cgt cta      683
Leu Met Phe His Gly Phe Gly Ala Val Arg Asp Glu Gly Phe Arg Leu
             35                      40                      45 ttt att caa atg agt aac cgg ctg atg gaa aac ggg att gct gct gtg      731
Phe Ile Gln Met Ser Asn Arg Leu Met Glu Asn Gly Ile Ala Ala Val
     50                      55                      60 cgc ttt gat ttt ggt tgt cat gga gaa agc gat ggt gaa ttt gag gac      779
Arg Phe Asp Phe Gly Cys His Gly Glu Ser Asp Gly Glu Phe Glu Asp
 65                      70                      75                      80 ttt acg ttc agc cag gag ctg aat gaa ggt tcg gca ttg att gat gct      827
Phe Thr Phe Ser Gln Glu Leu Asn Glu Gly Ser Ala Leu Ile Asp Ala
             85                      90                      95 gtt aag tcg atg tcg ttt gtg gat tcg aca aag ttt tca ttg ctg ggc      875
Val Lys Ser Met Ser Phe Val Asp Ser Thr Lys Phe Ser Leu Leu Gly
            100                     105                     110 gaa agc ctg ggt agt gtt gca gca agt att gtg gcc ggc aaa cga tcg      923
Glu Ser Leu Gly Ser Val Ala Ala Ser Ile Val Ala Gly Lys Arg Ser
            115                     120                     125 aca gag cta act tca ttg tgt atg tgg tca cca gca gca tcg ttc cta      971
Thr Glu Leu Thr Ser Leu Cys Met Trp Ser Pro Ala Ala Ser Phe Leu
        130                     135                     140 gat gaa ata ttg aac gat cac acc tta caa ggg aag acc gtg gat aat     1019
Asp Glu Ile Leu Asn Asp His Thr Leu Gln Gly Lys Thr Val Asp Asn
145                     150                     155                     160 gtc gaa aaa gac ggt tac ttt gat ttt tat gga ttg aag ttg ggg aaa     1067
Val Glu Lys Asp Gly Tyr Phe Asp Phe Tyr Gly Leu Lys Leu Gly Lys
                    165                     170                     175 gca ttc ttt gat gat ttg aaa aat atc aat att ttc gat aat gcc aaa     1115
Ala Phe Phe Asp Asp Leu Lys Asn Ile Asn Ile Phe Asp Asn Ala Lys
                180                     185                     190 aag tat caa ggt cca gta aaa atc gtg tat ggt act aat gat ttt atc     1163
Lys Tyr Gln Gly Pro Val Lys Ile Val Tyr Gly Thr Asn Asp Phe Ile
            195                     200                     205 cca gaa aaa tat tcg cat aag tat atg gat ggt tat gaa aat ggt gag     1211
Pro Glu Lys Tyr Ser His Lys Tyr Met Asp Gly Tyr Glu Asn Gly Glu
210                     215                     220 ctg gtg att gtg cag gat ggt gat cat ggc tgg caa agc gtt cca agc     1259
Leu Val Ile Val Gln Asp Gly Asp His Gly Trp Gln Ser Val Pro Ser
225                     230                     235                     240 cgg aaa cgg atc tta gat gaa act atg aaa ttc ttc cgt aaa acg ttg     1307
Arg Lys Arg Ile Leu Asp Glu Thr Met Lys Phe Phe Arg Lys Thr Leu
                    245                     250                     255 tta gaa gca aaa tag gtttacgtaa caaagctacc aagaggtaaa ggtaattaag     1362
Leu Glu Ala Lys   *
            260 gagacattta a atg gca tta gca aga gta gaa ttc ttt tcg cat tcc ctg    1412
             Met Ala Leu Ala Arg Val Glu Phe Phe Ser His Ser Leu
                                     265                     270 ttt aga atc act gaa tta acc gtt gtg att cca aat gat ttt gac cca     1460
Phe Arg Ile Thr Glu Leu Thr Val Val Ile Pro Asn Asp Phe Asp Pro
    275                     280                     285 gaa atg act aaa caa tat cca gaa gcg tat gcg cgt gcc ccc aaa ctt     1508
Glu Met Thr Lys Gln Tyr Pro Glu Ala Tyr Ala Arg Ala Pro Lys Leu
290                     295                     300                     305 cta gtg ttg tta cac ggc tat act ggg aac act gga gcg tgg ctg agt     1556
Leu Val Leu Leu His Gly Tyr Thr Gly Asn Thr Gly Ala Trp Leu Ser
            310                     315                     320 ggt ggc ttg atc act gat ctg gcg caa aaa tat aat ttg tat gta gtc     1604
Gly Gly Leu Ile Thr Asp Leu Ala Gln Lys Tyr Asn Leu Tyr Val Val
```

-continued

|   |   |   |   |   |   |   |   |   |   |   |   |   |   |   |   |      |
|---|---|---|---|---|---|---|---|---|---|---|---|---|---|---|---|------|
|   |   |   |   | 325 |   |   |   | 330 |   |   |   | 335 |   |   |   |      |
| tgc | cca | caa | ggc | gaa | aat | agt | ttc | tat | acg | gat | cac | aaa | cgt | gaa | ggt | 1652 |
| Cys | Pro | Gln | Gly | Glu | Asn | Ser | Phe | Tyr | Thr | Asp | His | Lys | Arg | Glu | Gly |      |
|   |   |   |   | 340 |   |   |   | 345 |   |   |   | 350 |   |   |   |      |
| ggt | aaa | tat | tgt | cag | ttc | gtt | gga | gat | gaa | gtg | gtg | cgt | tat | gcc | aaa | 1700 |
| Gly | Lys | Tyr | Cys | Gln | Phe | Val | Gly | Asp | Glu | Val | Val | Arg | Tyr | Ala | Lys |      |
|   | 355 |   |   |   |   | 360 |   |   |   |   | 365 |   |   |   |   |      |
| aag | act | ttt | ggg | tta | ccc | gat | gat | act | gaa | acg | atc | att | ggg | ggg | atg | 1748 |
| Lys | Thr | Phe | Gly | Leu | Pro | Asp | Asp | Thr | Glu | Thr | Ile | Ile | Gly | Gly | Met |      |
| 370 |   |   |   |   | 375 |   |   |   |   | 380 |   |   |   |   | 385 |      |
| tcg | atg | ggt | gga | ttt | ggt | gcc | att | cat | gtt | ggc | ttg | gct | tac | cca | gag | 1796 |
| Ser | Met | Gly | Gly | Phe | Gly | Ala | Ile | His | Val | Gly | Leu | Ala | Tyr | Pro | Glu |      |
|   |   |   |   | 390 |   |   |   | 395 |   |   |   | 400 |   |   |   |      |
| acc | ttc | agc | aaa | atc | ttt | gcg | ctt | tca | tcg | gca | ctg | atc | att | cat | aac | 1844 |
| Thr | Phe | Ser | Lys | Ile | Phe | Ala | Leu | Ser | Ser | Ala | Leu | Ile | Ile | His | Asn |      |
|   | 405 |   |   |   |   | 410 |   |   |   |   | 415 |   |   |   |   |      |
| att | gat | cac | atg | aag | tca | ggg | aca | gtc | gac | acc | att | ggt | gct | tct | aaa | 1892 |
| Ile | Asp | His | Met | Lys | Ser | Gly | Thr | Val | Asp | Thr | Ile | Gly | Ala | Ser | Lys |      |
|   |   |   | 420 |   |   |   |   | 425 |   |   |   |   | 430 |   |   |      |
| gac | tat | tat | caa | gat | gtg | ttt | ggt | gat | tta | gac | aag | gtg | gtt | gaa | agt | 1940 |
| Asp | Tyr | Tyr | Gln | Asp | Val | Phe | Gly | Asp | Leu | Asp | Lys | Val | Val | Glu | Ser |      |
|   | 435 |   |   |   |   | 440 |   |   |   |   | 445 |   |   |   |   |      |
| gaa | aat | aac | cct | gaa | gtt | cag | ttg | ttg | gaa | ctc | caa | aag | aat | gga | act | 1988 |
| Glu | Asn | Asn | Pro | Glu | Val | Gln | Leu | Leu | Glu | Leu | Gln | Lys | Asn | Gly | Thr |      |
| 450 |   |   |   |   | 455 |   |   |   |   | 460 |   |   |   |   | 465 |      |
| aag | att | cca | tca | atg | tat | tta | gca | tgc | ggt | tcg | gag | gac | ttt | cta | cat | 2036 |
| Lys | Ile | Pro | Ser | Met | Tyr | Leu | Ala | Cys | Gly | Ser | Glu | Asp | Phe | Leu | His |      |
|   |   |   | 470 |   |   |   |   | 475 |   |   |   |   | 480 |   |   |      |
| gaa | gag | aat | atg | aca | ttc | gtg | tcg | ttc | atg | aaa | caa | cat | ggc | att | gat | 2084 |
| Glu | Glu | Asn | Met | Thr | Phe | Val | Ser | Phe | Met | Lys | Gln | His | Gly | Ile | Asp |      |
|   |   |   | 485 |   |   |   |   | 490 |   |   |   |   | 495 |   |   |      |
| ttt | acc | tat | gag | gaa | gat | cat | ggc | att | cat | gat | ttt | aag | ttc | tgg | aat | 2132 |
| Phe | Thr | Tyr | Glu | Glu | Asp | His | Gly | Ile | His | Asp | Phe | Lys | Phe | Trp | Asn |      |
|   |   | 500 |   |   |   |   | 505 |   |   |   |   | 510 |   |   |   |      |
| cca | ttt | gct | gac | cgc | gca | atg | gaa | agt | tta | ctt | tcg | aag | taa |   |   | 2174 |
| Pro | Phe | Ala | Asp | Arg | Ala | Met | Glu | Ser | Leu | Leu | Ser | Lys | *   |   |   |      |
| 515 |   |   |   |   | 520 |   |   |   |   | 525 |   |   |   |   |   |      | gctagaaact aattataagt atcaaaaatc aaagcatccc ccacctagta aaacctgggt      2234 aggggatgct ttattatggt cgaaataggg tagaggtgag tgattgattg taggcaacgt      2294 ggccttattt gaaatagttg aggcaacatg taggaccttc tttctaaaat gactgagtga      2354 caaaatttgg atcggtgggg atgcatgtta gttacctgcc aaaatggggc gtcctagcat      2414 gatgtgatgc tgtaagtagt caggccatac cagagataaa tcaagagcgg tatgcgccat      2474 gttcaccagt gcctgtgtgc gttgaggctc gatc                                 2508

<210> SEQ ID NO 2
<211> LENGTH: 783
<212> TYPE: DNA
<213> ORGANISM: Lactobacillus buchneri
<220> FEATURE:
<221> NAME/KEY: misc_feature
<222> LOCATION: (0)...(0)
<223> OTHER INFORMATION: Sequence ORF1 from SEQ ID NO: 1

<400> SEQUENCE: 2
atgatcaaat ttgtaactac tgaaatcaat ggattaacgc ttagaggcac agctcatgtt       60
ccagatggtg aaccaggaca gcagtttcca acggtcttaa tgtttcatgg atttggagct      120
gttagggatg aaggcttccg tctatttatt caaatgagta accggctgat ggaaaacggg      180

-continued

```
attgctgctg tgcgctttga ttttggttgt catggagaaa gcgatggtga atttgaggac    240
tttacgttca gccaggagct gaatgaaggt tcggcattga ttgatgctgt taagtcgatg    300
tcgtttgtgg attcgacaaa gttttcattg ctgggcgaaa gcctgggtag tgttgcagca    360
agtattgtgg ccggcaaacg atcgacagag ctaacttcat tgtgtatgtg gtcaccagca    420
gcatcgttcc tagatgaaat attgaacgat cacaccttac aagggaagac cgtggataat    480
gtcgaaaaag acggttactt tgattttat ggattgaagt tggggaaagc attctttgat    540
gatttgaaaa atatcaatat tttcgataat gccaaaaagt atcaaggtcc agtaaaaatc    600
gtgtatggta ctaatgattt tatcccagaa aaatattcgc ataagtatat ggatggttat    660
gaaaatggtg agctggtgat tgtgcaggat ggtgatcatg gctggcaaag cgttccaagc    720
cggaaacgga tcttagatga aactatgaaa ttcttccgta aaacgttgtt agaagcaaaa    780
tag                                                                  783
```

<210> SEQ ID NO 3
<211> LENGTH: 260
<212> TYPE: PRT
<213> ORGANISM: Lactobacillus buchneri
<220> FEATURE:
<221> NAME/KEY: PEPTIDE
<222> LOCATION: (0)...(0)
<223> OTHER INFORMATION: Translation of ORF1 (SEQ ID NO: 2)

<400> SEQUENCE: 3

```
Met Ile Lys Phe Val Thr Thr Glu Ile Asn Gly Leu Thr Leu Arg Gly
 1               5                  10                  15

Thr Ala His Val Pro Asp Gly Glu Pro Gly Gln Gln Phe Pro Thr Val
            20                  25                  30

Leu Met Phe His Gly Phe Gly Ala Val Arg Asp Glu Gly Phe Arg Leu
        35                  40                  45

Phe Ile Gln Met Ser Asn Arg Leu Met Glu Asn Gly Ile Ala Ala Val
    50                  55                  60

Arg Phe Asp Phe Gly Cys His Gly Glu Ser Asp Gly Glu Phe Glu Asp
65                  70                  75                  80

Phe Thr Phe Ser Gln Glu Leu Asn Glu Gly Ser Ala Leu Ile Asp Ala
                85                  90                  95

Val Lys Ser Met Ser Phe Val Asp Ser Thr Lys Phe Ser Leu Leu Gly
            100                 105                 110

Glu Ser Leu Gly Ser Val Ala Ala Ser Ile Val Ala Gly Lys Arg Ser
        115                 120                 125

Thr Glu Leu Thr Ser Leu Cys Met Trp Ser Pro Ala Ala Ser Phe Leu
    130                 135                 140

Asp Glu Ile Leu Asn Asp His Thr Leu Gln Gly Lys Thr Val Asp Asn
145                 150                 155                 160

Val Glu Lys Asp Gly Tyr Phe Asp Phe Tyr Gly Leu Lys Leu Gly Lys
                165                 170                 175

Ala Phe Phe Asp Asp Leu Lys Asn Ile Asn Ile Phe Asp Asn Ala Lys
            180                 185                 190

Lys Tyr Gln Gly Pro Val Lys Ile Val Tyr Gly Thr Asn Asp Phe Ile
        195                 200                 205

Pro Glu Lys Tyr Ser His Lys Tyr Met Asp Gly Tyr Glu Asn Gly Glu
    210                 215                 220

Leu Val Ile Val Gln Asp Gly Asp His Gly Trp Gln Ser Val Pro Ser
225                 230                 235                 240

Arg Lys Arg Ile Leu Asp Glu Thr Met Lys Phe Phe Arg Lys Thr Leu
```

Leu Glu Ala Lys
            260

<210> SEQ ID NO 4
<211> LENGTH: 801
<212> TYPE: DNA
<213> ORGANISM: Lactobacillus buchneri
<220> FEATURE:
<221> NAME/KEY: misc_feature
<222> LOCATION: (0)...(0)
<223> OTHER INFORMATION: Sequence for ORF2 from SEQ ID NO: 1

<400> SEQUENCE: 4

```
atggcattag caagagtaga attcttttcg cattccctgt ttagaatcac tgaattaacc      60
gttgtgattc caaatgattt tgacccagaa atgactaaac aatatccaga agcgtatgcg     120
cgtgccccca aacttctagt gttgttacac ggctatactg gaacactgga gcgtggctg     180
agtggtggct tgatcactga tctggcgcaa aaatataatt tgtatgtagt ctgcccacaa     240
ggcgaaaata gtttctatac ggatcacaaa cgtgaaggtg gtaaatattg tcagttcgtt     300
ggagatgaag tggtgcgtta tgccaaaaag acttttgggt tacccgatga tactgaaacg     360
atcattgggg ggatgtcgat gggtggattt ggtgccattc atgttggctt ggcttaccca     420
gagaccttca gcaaaatctt tgcgctttca tcggcactga tcattcataa cattgatcac     480
atgaagtcag ggacagtcga caccattggt gcttctaaag actattatca agatgtgttt     540
ggtgatttag acaaggtggt tgaaagtgaa ataaccctg aagttcagtt gttggaactc      600
caaaagaatg gaactaagat tccatcaatg tatttagcat gcggttcgga ggactttcta     660
catgaagaga atatgacatt cgtgtcgttc atgaaacaac atggcattga ttttacctat     720
gaggaagatc atggcattca tgattttaag ttctggaatc catttgctga ccgcgcaatg     780
gaaagtttac tttcgaagta a                                               801
```

<210> SEQ ID NO 5
<211> LENGTH: 266
<212> TYPE: PRT
<213> ORGANISM: Lactobacillus buchneri
<220> FEATURE:
<221> NAME/KEY: PEPTIDE
<222> LOCATION: (0)...(0)
<223> OTHER INFORMATION: Translation of SEQ ID NO: 4

<400> SEQUENCE: 5

Met Ala Leu Ala Arg Val Glu Phe Phe Ser His Ser Leu Phe Arg Ile
 1               5                  10                  15

Thr Glu Leu Thr Val Val Ile Pro Asn Asp Phe Asp Pro Glu Met Thr
            20                  25                  30

Lys Gln Tyr Pro Glu Ala Tyr Ala Arg Ala Pro Lys Leu Leu Val Leu
        35                  40                  45

Leu His Gly Tyr Thr Gly Asn Thr Gly Ala Trp Leu Ser Gly Gly Leu
    50                  55                  60

Ile Thr Asp Leu Ala Gln Lys Tyr Asn Leu Tyr Val Val Cys Pro Gln
65                  70                  75                  80

Gly Glu Asn Ser Phe Tyr Thr Asp His Lys Arg Glu Gly Gly Lys Tyr
                85                  90                  95

Cys Gln Phe Val Gly Asp Glu Val Val Arg Tyr Ala Lys Lys Thr Phe
            100                 105                 110

Gly Leu Pro Asp Asp Thr Glu Thr Ile Ile Gly Gly Met Ser Met Gly
        115                 120                 125

```
Gly Phe Gly Ala Ile His Val Gly Leu Ala Tyr Pro Glu Thr Phe Ser
        130                 135                 140

Lys Ile Phe Ala Leu Ser Ser Ala Leu Ile Ile His Asn Ile Asp His
145                 150                 155                 160

Met Lys Ser Gly Thr Val Asp Thr Ile Gly Ala Ser Lys Asp Tyr Tyr
                165                 170                 175

Gln Asp Val Phe Gly Asp Leu Asp Lys Val Val Glu Ser Glu Asn Asn
                180                 185                 190

Pro Glu Val Gln Leu Leu Glu Leu Gln Lys Asn Gly Thr Lys Ile Pro
                195                 200                 205

Ser Met Tyr Leu Ala Cys Gly Ser Glu Asp Phe Leu His Glu Glu Asn
        210                 215                 220

Met Thr Phe Val Ser Phe Met Lys Gln His Gly Ile Asp Phe Thr Tyr
225                 230                 235                 240

Glu Glu Asp His Gly Ile His Asp Phe Lys Phe Trp Asn Pro Phe Ala
                245                 250                 255

Asp Arg Ala Met Glu Ser Leu Leu Ser Lys
                260                 265

<210> SEQ ID NO 6
<211> LENGTH: 246
<212> TYPE: PRT
<213> ORGANISM: Butyrivibrio fibrisolvens
<220> FEATURE:
<221> NAME/KEY: PEPTIDE
<222> LOCATION: (0)...(0)
<223> OTHER INFORMATION: CinI, Accession No: AAC44493.1

<400> SEQUENCE: 6

Met Tyr Ile Val Asp Asp Gly Ile Lys Leu Asn Ala Ile Leu Asp Met
1               5                   10                  15

Pro Glu Gly Gly Ala Glu Lys Cys Pro Leu Cys Leu Val Phe His Gly
                20                  25                  30

Phe Thr Gly His Ile Glu Glu Asp His Ile Val Ala Val Ala Lys Gly
        35                  40                  45

Leu Asn Glu Ile Gly Val Ala Thr Leu Arg Val Asp Leu Phe Gly His
50                  55                  60

Gly Lys Ser Glu Gly Glu Phe Arg Glu His Asn Leu Tyr Lys Trp Leu
65                  70                  75                  80

Asn Asn Ile Leu Ala Val Val Asp Tyr Ala Lys Lys Leu Asp Phe Val
                85                  90                  95

Thr Asp Leu Tyr Ile Cys Gly His Ser Gln Gly Gly Leu Ala Val Thr
                100                 105                 110

Leu Ala Ala Ala Met Glu Arg Asp Thr Ile Lys Ala Leu Met Pro Leu
        115                 120                 125

Ser Pro Ala Tyr Val Ile Ile Asp Gly Ala Lys Ala Gly Met Leu Leu
130                 135                 140

Gly Gln Pro Phe Asp Pro Glu His Ile Pro Asp Glu Leu Val Ser Trp
145                 150                 155                 160

Asp Gly Arg Thr Leu Asn Gly Asn Tyr Ile Arg Val Ala Gln Ser Ile
                165                 170                 175

Asp Leu Asp Ala Ala Met Lys Lys Phe Thr Gly Pro Val Leu Ile Val
                180                 185                 190

His Gly Asp Ala Asp Asp Thr Val Pro Val Glu Phe Ala Ile Asp Ala
        195                 200                 205

Ser Lys Lys Phe Ala Asn Cys Lys Leu Glu Leu Ile Lys Asp Asp Asp
```

```
                    210                 215                 220

His Cys Tyr Gly Lys His Met Asp Leu Met Val Lys Ala Val Gln Glu
225                 230                 235                 240

Phe Val Arg Lys Leu Ile
                245

<210> SEQ ID NO 7
<211> LENGTH: 285
<212> TYPE: PRT
<213> ORGANISM: Butyrivibrio fibrisolvens
<220> FEATURE:
<221> NAME/KEY: PEPTIDE
<222> LOCATION: (0)...(0)
<223> OTHER INFORMATION: Cin II, Accession No: AAB57776.1

<400> SEQUENCE: 7

Met Lys Lys Gly Val Phe Thr Leu Leu Thr Ala Ser Leu Cys Leu Leu
  1               5                  10                  15

Ala Ala Cys Gly Thr Ser Ser Asn Ser Ser Lys Glu Ile Val Met Lys
                 20                  25                  30

Ser Asp Tyr Thr Val Asn Thr Glu Val Val Glu Ile Pro Ser Gly Asp
             35                  40                  45

Asn Thr Leu Tyr Gly Thr Leu Tyr Thr Pro Glu Thr Asp Ser Lys Thr
         50                  55                  60

Pro Leu Ile Ile Met Cys His Gly Tyr Asn Gly Val Gly Asp Asp Phe
 65                  70                  75                  80

Gln Glu Glu Gly Lys Tyr Phe Ala Gln Asn Gly Ile Ala Thr Tyr Thr
                 85                  90                  95

Leu Asp Phe Cys Gly Gly Ser Thr Arg Ser Lys Ser Thr Gly Glu Thr
            100                 105                 110

Lys Asp Met Thr Ile Phe Thr Glu Lys Ala Asp Leu Leu Asn Ala Tyr
        115                 120                 125

Asn Tyr Phe Lys Thr Gln Asp Asn Ile Asp Asn Asn Asn Ile Phe Leu
130                 135                 140

Phe Gly Gly Ser Gln Gly Gly Leu Val Thr Thr Leu Ala Thr Glu Glu
145                 150                 155                 160

Leu Gly Asp Glu Val Ala Gly Met Ala Leu Tyr Phe Pro Ala Leu Cys
                165                 170                 175

Ile Ala Asp Asn Trp Arg Glu Thr Phe Pro Glu Thr Asp Met Ile Pro
            180                 185                 190

Lys Glu Glu Glu Phe Trp Gly Met Thr Leu Gly Lys Asn Phe Phe Glu
        195                 200                 205

Ser Ile His Asp Phe Asp Val Phe Ser Glu Ile Gly Ser Tyr Pro Asn
210                 215                 220

Asn Val Leu Ile Leu His Gly Asp Lys Asp Glu Ile Val Pro Leu Ser
225                 230                 235                 240

Tyr Ser Glu Lys Ala Ala Ser Ile Tyr Glu His Ala Lys Leu Ile Val
                245                 250                 255

Met Glu Gly Glu Gly His Gly Phe Ala Pro Glu Ala Ala Lys Thr Ala
            260                 265                 270

Arg Glu Asp Val Leu Ser Phe Met Lys Glu Asn Ile Arg
        275                 280                 285
```

Cloning and Sequencing of the Ferulate Esterase Gene from Lactobacillus
Buchneri LN4017
Smiley, et al.  Atty Docket No. 2278
Figure 1/5

Percent Similarity: 39.918   Percent Identity: 27.160

```
SEQ ID NO: 3      1 ................................MIKFVTTEINGLT  13
                                                            . |           |
SEQ ID NO: 7      1 MKKGVFTLLTASLCLLAACGTSSNSSKEIVMKSDYTVNTEVVEIPSGDNT  50

SEQ ID NO: 3     14 LRGTAHVPDGEPGQQFPTVLMFHGFGAVRDEGFRLFIQMSNRLMENGIAA  63
                    | || : |   |   . | ::| ||:  | |:    | :       :||||
SEQ ID NO: 7     51 LYGTLYTP..ETDSKTPLIIMCHGYNGVGDD....FQEEGKYFAQNGIAT  94

SEQ ID NO: 3     64 VRFDFGCHG....ESDGEFEDFTFSQELNEGSALIDAVKSMSFVDSTKFS 109
                    | | |  |      .| || .| |    | :     . |.   :|.
SEQ ID NO: 7     95 YTLDF.CGGSTRSKSTGETKDMTIFTEKADLLNAYNYFKTQDNIDNNNIF 143

SEQ ID NO: 3    110 LLGESLGSVAASIVAGKRSTELTSLCMWSPAASFLDEILNDHTLQGKTVD 159
                    | | | | | . .:  .   |. : ::  ||      |  |    .| |
SEQ ID NO: 7    144 LFGGSQGGLVTTLATEELGDEVAGMALYFPALCIAD...NWRETFPET.D 189

SEQ ID NO: 3    160 NVEKDGYFDFYGLKLGKAFFDDLKNINIFDNAKKYQGPVKIVYGTND.FI 208
                    : |:      :|:|: ||| ||: . . .:|     |  | |.:|  | :
SEQ ID NO: 7    190 MIPKEE..EFWGMTLGKNFFESIHDFDVFSEIGSYPNNVLILHGDKDEIV 237

SEQ ID NO: 3    209 PEKYSHKYMDGYENGELVIVQDGDHGWQSVPSRKRILDETMKFFRKTLLE 258
                    |   || |      ||. .|::.:  |||. .  . |    :: : | :. :
SEQ ID NO: 7    238 PLSYSEKAASIYEHAKLIVMEGEGHGF.APEAAKTAREDVLSFMKENIR. 285
```

Cloning and Sequencing of the Ferulate Esterase Gene from Lactobacillus
Buchneri LN4017
Smiley, et al.          Atty Docket No. 2278
Figure 2/5

```
Percent Similarity: 37.295   Percent Identity: 27.049

.         .         .         .         .
SEQ ID NO: 3     1 MIKFVTTEINGLTLRGTAHVPDGEPGQQFPTVLMFHGFGAVRDEGFRLFI 50
                        .|: |     .|:|    :. |  |.|.||     :|      :
SEQ ID NO: 6     1 ....MYIVDDGIKLNAILDMPEG.GAEKCPLCLVFHGFTGHIEEDH..IV 43

.         .         .         .         .
SEQ ID NO: 3    51 QMSNRLMENGIAAVRFDFGCHGESDGEFEDFTFSQELNEGSALIDAVKSM 100
                    ..  |  |:| .|  |    ||.|:|||  :     . ||    |.:|  | :
SEQ ID NO: 6    44 AVAKGLNEIGVATLRVDLFGHGKSEGEFREHNLYKWLNNILAVVDYAKKL 93

.         .         .         .         .
SEQ ID NO: 3   101 SFVDSTKFSLLGE S LGSVAASIVAGKRSTELTSLCMWSPAASFLDEILND 150
                   ||   |   : | |‖|  .| .:  |        : .|    |||     :|
SEQ ID NO: 6    94 DFV..TDLYICGH S QGGIAVTLAAAMERDTIKALMPLSPAYVIIDG.AKA 140

.         .         .         .         .
SEQ ID NO: 3   151 HTLQGKTVDNVE.KDGYFDFYGLKLGKAFFDDLKNINIFDNAKKYQGPVK 199
                     | |.  |     |     . |   |      :    ...|.:   ||: |||
SEQ ID NO: 6   141 GMLLGQPFDPEHIPDELVSWDGRTLNGNYIRVAQSIDLDAAMKKFTGPVL 190

.         .         .         .         .
SEQ ID NO: 3   200 IVYG.TN D FIPEKYSHKYMDGYENGELVIVQDGD H GWQSVPSRKRILDET 248
                   ||:|    .|| :| .:.         : | .| ::.| ‖| :         ..
SEQ ID NO: 6   191 IVHGDAD D FVPVEFAIDASKKFANCKLELIKDDD H CYGK..HMDLMVKAV 238

.
SEQ ID NO: 3   249 MKFFRKTLLEAK 260
                    .|  || :
SEQ ID NO: 6   239 QEFVRKLI.... 246
```

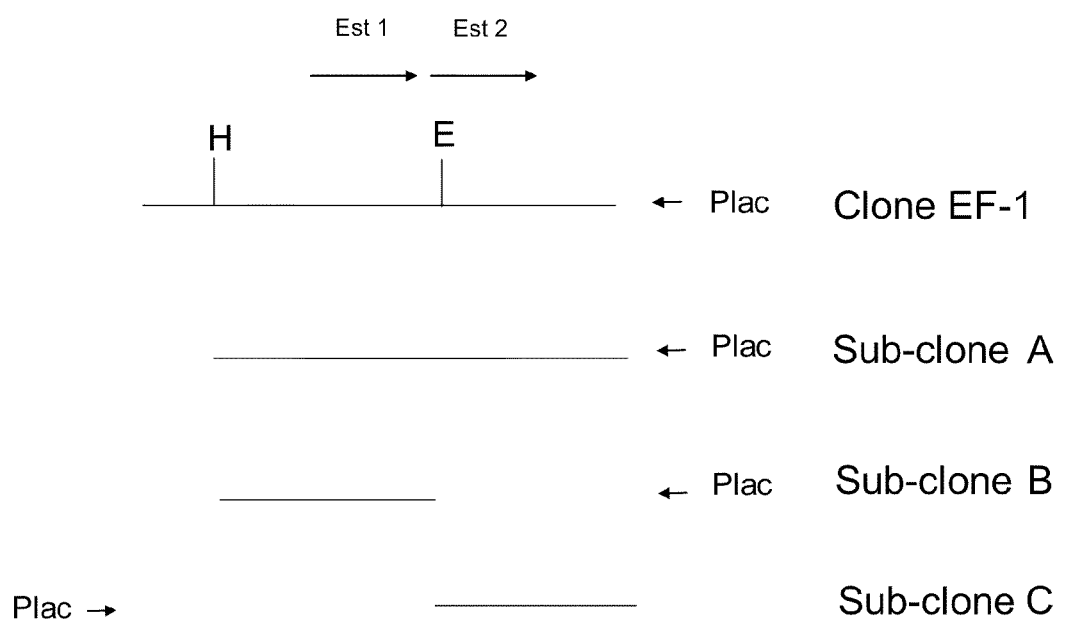
Figure 3/5

Figure 4

Percent Similarity: 32.780   Percent Identity: 22.822

```
SEQ ID NO: 3      1 ....MIKFVTTEINGLTLRGTAHVP...DGEPGQQFP........TVLMF  35
                    :.| . : :|   |  :|   | |  .|:|         ..:
SEQ ID NO: 5      1 MALARVEFFSHSLFRIT.ELTVVIPNDFDPEMTKQYPEAYARAPKLLVLL 49

SEQ ID NO: 3     36 HGF....GAVRDEGFRLFIQMSNRLMENGIAAVRFDFGCHGESDGEFEDF 81
                    ||:    ||    |    :    |       :  |    |.: |
SEQ ID NO: 5     50 HGYTGNTGAWLSGGLITDLAQKYNLYVVCPQGENSFYTDHKREGGKYCQF 99

SEQ ID NO: 3     82 TFSQELNEGSALIDAVKSMSFVDSTKFSLLGE S LGSVAASIVAGKRSTEL 131
                    : .        | |.    | |.  : ||:|   |   |   |
SEQ ID NO: 5    100 VGDEVVRY......AKKTFGLPDDTETIIGGM S MGGFGA.IHVGLAYPET 142

SEQ ID NO: 3    132 TSLCMWSPAASFLDEILNDHTLQGKTVDNV..EKDGYFDFYGLKLGKAFF 179
                    |     .| : | ||   |  |||: ||| | :|  | |
SEQ ID NO: 5    143 FSKIFALSSALIIHNI..DHMKSG.TVDTIGASKDYYQDVFG.DLDKVVE 188

SEQ ID NO: 3    180 D....DLKNINIFDNAKKYQGPVKIVYGTN D FIPEKYSHKYMDGYENGEL 225
                    :...:  :  | |  . :  |  .| ||:  . .. :.   |
SEQ ID NO: 5    189 SENNPEVQLLELQKNGTKIPS.MYLACGSE D FLHEE.NMTFVSFMKQHGI 236

SEQ ID NO: 3    226 VIVQDGD H GWQSVPSRKRILDETMKFFRKTLLEAK 260
                    :  |||      | |.
SEQ ID NO: 5    237 DFTYEED H GIHDFKFWNPFADRAMESLLSK..... 266
```

Figure 5

Percent Similarity: 33.043   Percent Identity: 23.913

```
SEQ ID NO: 6      1 ....................MYIVDDGIKLNAILDMPEGGAEKCPLCLVFH  31
                                         ::  .        ||  |     |  ..  |
SEQ ID NO: 5      1 MALARVEFFSHSLFRITELTVVIPNDFDPEMTKQYPEAYARAPKLLVLLH  50

SEQ ID NO: 6     32 GFTGH....IEEDHIVAVAKGLNEIGVATLRVDLF..GHGKSEGEFREHN  75
                    |:||.   :    |  .|.  |    |      .  |    |  :   |.:
SEQ ID NO: 5     51 GYTGNTGAWLSGGLITDLAQKYNLYVVCPQGENSFYTDHKREGGKY....  96

SEQ ID NO: 6     76 LYKWLNNILAVVDYAKK...LDFVTDLYICGHSQGGLAVTLAAAMERDTI 122
                    ... .    || ||||   |    |:  | |||  ||             :|
SEQ ID NO: 5     97 .CQFVGD..EVVRYAKKTFGLPDDTETIIGGMSMGGFGAIHVGLAYPETF 143

SEQ ID NO: 6    123 KALMPLSPAYVI..IDGAKAGMLLGQPFDPEHIPDELVSWDGRTLNGNYI 170
                    :   || | :|   ||    |.|.         ::    |       .  |
SEQ ID NO: 5    144 SKIFALSSALIIHNIDHMKSGTVDTIGASKDYYQDVFGDLDKVVESENNP 193

SEQ ID NO: 6    171 RVAQSIDLDAAMKKFTGPVLIVHGDADDTVPVEFAIDASKKFANCKLELI 220
                    |  | ::|        |    | :.   ..:|.   |        |    ::
SEQ ID NO: 5    194 EV.QLLELQKNGTKI..PSMYLACGSEDFLHEENMTFVS.FMKQHGIDFT 239

SEQ ID NO: 6    221 KDDDHCYGKHMDLMVKAVQEFVRKLI...... 246
                    ::|| |  |    |     |    |  : .
SEQ ID NO: 5    240 YEEDH..GIH.DF..KFWNPFADRAMESLLSK 266
```

CLONING AND SEQUENCING OF THE FERULATE ESTERASE GENE FROM *LACTOBACILLUS BUCHNERI* LN4017

CROSS-REFERENCE TO RELATED APPLICATIONS

This application claims the benefit of U.S. Provisional Application No. 60/865,492 filed Nov. 13, 2007.

FIELD OF THE INVENTION

The present invention relates to polypeptides having ferulate esterase activity and the nucleic acid sequences that encode them, and methods of use to enhance cell wall digestibility in plants.

BACKGROUND OF THE INVENTION

The plant cell wall is a complex structure consisting of different polysaccharides, the major components being cellulose, hemicelluloses and pectins. These polysaccharides may be cross-linked, or linked to lignin by phenolic acid groups such as ferulic acid. Ferulic acid may play a role in the control of cell wall growth in the plant and ferulic acid cross-linking within the cell wall is believed to restrict cell wall digestion by microorganisms (Fry et al., (1983) *Planta* 157: 111-123; and Borneman et al., (1990) *Appl. Microbial. Biotechnol.* 33: 345-351). The resistance of the plant cell wall to digestion presents significant challenges in the animal production industry. Some microorganisms are known to exhibit ferulic acid esterase activity (ferulate esterase) and thereby facilitate the breakdown of plant cell walls and fiber digestion (U.S. Pat. No. 6,143,543).

Plant cell walls contain a range of alkali-labile ester-linked phenolic acids. In particular, grass cell walls are characterized by the presence of large amounts of esterified ferulic and p-coumaric acids (mainly in their E configurations), linked to arabinoxylans at the C5 of arabinose. These are released as ferulated oligosaccharides (FAX and PAX) by cellulase treatment but in vivo provide a substrate for peroxidase-catalyzed cross-linking of cell wall polysaccharides and lignin. The high levels of these phenolic acids and their dimers have a dramatic influence on the mechanical properties, digestibility and rates of digestion of grasses by ruminants.

It has been shown that ferulic acid is the predominant p-hydroxycinnamic acid esterified to grass polysaccharide. Dehydrodiferulate dimers and cyclobutane-type dimer mixtures have been isolated from plant cell walls (Waldron, et al., (1996) *Phytochemical Analysis* 7:305). These mixtures are present in large amounts in grass cells. Ether linked ferulic acid-coniferyl alcohol dimers, have also been isolated from cell walls (Jacquet, et al., (1996) *Polyphenol Comm.* Bordeaux pp 451) establishing that ferulate esters are oxidatively co-polymerized with lignin precursors which may anchor lignins to cell wall polysaccharides. The yield of these dimers in grass cells indicates that phenolic dehydrodimer cross-linking of cell wall polysaccharides is much more extensive than was previously thought.

An enzyme system has been reported from parsley endomembranes that catalyses the ferulation of endogenous polysaccharide acceptors from feruloyl CoA, pointing to the ER/golgi as the site of polysaccharide esterification and the CoA ester as the physiological co-substrate (Meyer, et al., (1991) *FEBS Lett.* 290:209). Further evidence for this has been found in water-soluble extracellular polysaccharides excreted in large amounts into the medium by grass cell cultures. This material is highly esterified with ferulic and p-coumaric acid at levels similar to the cell walls of the cultured cells.

Ferulate esterase activity has been detected in several fungal species including, anaerobic gut fungi, yeasts, actinomycetes, and a few fiber-degrading ruminal bacteria, which enables them to de-esterify arabinoxylans and pectins.

Presently in livestock agriculture, while a high-forage diet is desirable, it does not currently satisfy the demands of modern animal production. Fiber digestion is a limiting factor to dairy herd milk yield and composition, and to beef production in beef operations feeding a high forage diet, and hence restricts profitability of farmers. Enhancing fiber digestion has a dual impact: 1) the animal eats more due to a reduced gut fill and therefore produces more, and 2) the animal gets more out of what it eats since the fiber is more digestible. Ultimately, these changes should increase milk yield, in dairy cows, and beef production in forage fed animals. Farmers either have to choose whether to tolerate a lower level of feed digestibility and hence productivity, or they can choose to use inoculants, forage additives or other amendments that improve the digestibility of feed.

Accordingly, farmers can treat ensiled feed or other animal feed with fiber degrading enzymes, originating mainly from molds, to improve digestibility of feed. In addition, there are several commercially available *Saccharomyces cerevisiae* yeast strains that when fed to cattle reportedly improve fiber digestion (Erasmus et al., (1992) *J. Dairy Sci.* 75: 3056-3065; and Wohlt et al., (1998) *J. Dairy Sci.* 81: 1345-1352). Another alternative approach to improving fiber digestion is the provision of a diet inherently possessing good digestibility characteristics. For corn silage, this may include brown midrib corn silage (Oba and Allen, (1999) *J. Dairy Sci.* 82: 135-142), or alternatively, corn hybrids recognized as being highly digestible. Further, new technologies incorporate fungal gene(s) responsible for the production of ferulate esterase into plant tissue for subsequent expression, resulting in improvements in fiber digestibility (WO 02/68666).

Generally, for an animal to make efficient use of the feed it consumes, the energy demands of the microorganisms in the digestive tract must be met and synchronized with the availability of plant proteins. A lack of synchrony will lead to a) proteins and other nutrients being poorly utilized in the digestive tract, b) a loss of nitrogen, in urine and feces and c) a need to feed excessive amounts of protein concentrates as supplements to the diet. The use of organisms and enzymes can improve or enhance the value of the feed animals receive and the performance of the animals. For example, WO 92/10945 discloses such a combination for use in enhancing the value of prepared silage. WO 93/13786 and WO 96/17525 relate to the enhancement of animal performance using microorganisms, while WO 93/3786 refers to a species of *Lactobacillus*. Further, it has been shown that *Lactobacillus buchneri* is suitable as a direct fed microbial to increase an animal's performance (U.S. Pat. No. 6,699,514).

BRIEF SUMMARY OF THE INVENTION

Provided herein are compositions and methods for improving feed digestibility. One embodiment provides a DNA construct comprising a promoter that drives expression in a plant or plant cell, operably linked to a nucleotide sequence that encodes a polypeptide having ferulate esterase activity, wherein the nucleotide sequence is a polynucleotide comprising SEQ ID NO: 1, 2 or 4, or a polynucleotide with at least about 85% sequence identity to SEQ ID NO: 1, 2 or 4, such as a polynucleotide encoding SEQ ID NO: 3 or 5, or a polynucleotide encoding a polypeptide having at least 85% sequence identity to SEQ ID NO: 3 or 5. The nucleotide sequence of the construct may be derived from *Lactobacillus buchneri* or from other microbial sources, or it may be an engineered sequence that has been optimized, shuffled, or otherwise subjected to engineered variation. The DNA construct may or may not include signal peptides or targeting sequences.

Another embodiment is a transformed plant or plant cell comprising the DNA construct described above. Such plants or plant cells may be monocot plants or cells, or dicot plants or cells. Particularly, such plants or plant cells may include plants or cells from *Festuca, Lolium, Sorghum, Zea, Triticum, Avena*, and *Poa*. Such plants may display increased digestibility. Seeds of these plants that comprise the DNA construct are also embodiments of the invention. Additional embodiments include such transgenic plants as described above which also comprise an introduced DNA sequence encoding a xylanase.

Further embodiments include a method of controlling the level of phenolic acid cross-linking in plant cell walls of a transgenic plant, the method comprising introducing into the plant a DNA construct comprising a promoter that drives expression in a plant or plant cell, operably linked to a nucleotide sequence that encodes a polypeptide having ferulate esterase activity, wherein the nucleotide sequence is a polynucleotide comprising SEQ ID NO: 1, 2 or 4, or a polynucleotide with at least about 85% sequence identity to SEQ ID NO: 1, 2 or 4, such as a polynucleotide encoding SEQ ID NO: 3 or 5, or a polynucleotide encoding a polypeptide having at least 85% sequence identity to SEQ ID NO: 3 or 5. Transgenic plants, plant parts and seeds produced by such a method are also encompassed by the embodiments.

Another embodiment is a method for increasing digestibility of a plant or plant part fed to an animal, the method comprising introducing into a plant a DNA construct comprising a promoter that drives expression in a plant or plant cell, operably linked to a nucleotide sequence that encodes a polypeptide having ferulate esterase activity, wherein the nucleotide sequence is a polynucleotide comprising SEQ ID NO: 1, 2 or 4, or a polynucleotide with at least about 85% sequence identity to SEQ ID NO: 1, 2 or 4, such as a polynucleotide encoding SEQ ID NO: 3 or 5, or a polynucleotide encoding a polypeptide having at least 85% sequence identity to SEQ ID NO: 3 or 5. Transgenic plants, plant parts and seeds produced by such a method are also encompassed by the embodiments.

The embodiments also include isolated polypeptides comprising the amino acid sequence set forth in SEQ ID NOs: 3 or 5; or a polypeptide having at least 85% sequence identity to SEQ ID NOs: 3 or 5, wherein the polypeptide has ferulate esterase activity. Furthermore, the embodiments include isolated nucleic acid molecules, including a polynucleotide comprising the sequence set forth in SEQ ID NOs: 1, 2 or 4; a polynucleotide having at least about 85% sequence identity to SEQ ID NOs: 1, 2 or 4; a polynucleotide encoding the amino acid sequence of SEQ ID NOs: 3 or 5; and a polynucleotide encoding the amino acid sequence of a polypeptide having at least 85% sequence identity to SEQ ID NOs: 3 or 5, wherein said polypeptide has ferulate esterase activity.

BRIEF DESCRIPTION OF THE DRAWINGS

FIG. 1: GAP alignment of SEQ ID NO: 3 with CinII (SEQ ID NO: 7) from *Butyrivibrio fibrisolvens* (AAB57776.1) showing conservation of the catalytic triad.

FIG. 2: GAP alignment of SEQ ID NO: 3 with Cin I (SEQ ID NO: 6) from *Butyrivibrio fibrisolvens* (AAC44493.1) showing conservation of the catalytic triad.

FIG. 3: Map of the region sub-cloned for sequence analysis. Deletions were constructed by using convenient restriction enzymes to digest and re-ligate or to generate fragments for sub-cloning. The direction of transcription by the plasmid borne lac promoter is indicated for each plasmid. The direction of translation of open reading frames (ORFs) identified from the DNA sequence is indicated by arrows. Restriction enzyme sites are shown as follows: H, HindIII; E, EcoRI.

FIG. 4: GAP alignment of SEQ ID NO: 3 with SEQ ID NO: 5 showing conservation of the catalytic triad.

FIG. 5: GAP alignment of SEQ ID NO: 5 with Cin I (SEQ ID NO: 6) from *Butyrivibrio fibrisolvens* (AAC44493.1) showing conservation of the catalytic triad.

DETAILED DESCRIPTION OF THE INVENTION

The present invention provides compositions and methods directed to producing ferulate esterase (FE) and acetyl esterase (AE) and using said FE to enhance silage plant fiber digestion in animals. The compositions are nucleotide and amino acid sequences for FE enzymes. Those of skill in the art are aware that FE is known by a number of different names, including, but not limited to, feruloyl esterase, cinnamoyl ester hydrolase, ferulic acid hydrolase, and hydroxycinnamoyl esterase. Changes in the naming of enzymes can occur frequently, so the International Union of Biochemistry and Molecular Biology (IUBMB) has a nomenclature system to standardize the names of enzymes by assigning numbers to them. The IUBMB number for the ferulate esterase (FE) referred to throughout this disclosure is EC 3.1.1.73. The IUBMB number for the acetyl esterase (AE) referred to throughout this disclosure is EC 3.1.3.6.

Specifically, the present invention provides FE polypeptides having the amino acid sequences set forth in SEQ ID NOs:3 and 5, and variants and fragments thereof. Nucleic acid molecules that were isolated from the strain of *Lactobacillus buchneri* designated LN4017, such as, for example, SEQ ID NO:1, and variants and fragments thereof, comprising nucleotide sequences that encode the amino acid sequences shown in SEQ ID NOs: 3 and 5 are further provided.

A deposit of the *Lactobacillus buchneri* LN4017 strain was previously made with the American Type Culture Collection (ATCC), 10801 University Blvd., Manassas, Va. 20110-2209 (ATCC Accession No. PTA-6138). These organisms were deposited on Aug. 3, 2004, as required for U.S. patent application Ser. No. 11/217,764, herein incorporated by reference. The microorganisms deposited with the ATCC were taken from the same deposit maintained at Pioneer Hi-Bred International, Inc (Des Moines, Iowa). Applicant(s) will meet all the requirements of 37 C.F.R. § 1.801-1.809, including providing an indication of the viability of the sample when the deposit is made. Each deposit will be maintained without restriction in the ATCC Depository, which is a public depository, for a period of 30 years, or 5 years after the most recent request, or for the enforceable life of the patent, whichever is longer, and will be replaced if it ever becomes nonviable during that period. However, it should be understood that the availability of a deposit does not constitute a license to practice the subject invention in derogation of patent rights granted by government action.

Nucleotide sequences that are optimized for expression in plants, and that encode the polypeptides of SEQ ID NOs: 3 and 5 can be generated using standard methods known in the art. Such plant-optimized nucleotide sequences are further encompassed by the present invention. Plants, plant cells, seeds, and microorganisms comprising a nucleotide sequence that encodes an FE polypeptide of the invention are also disclosed herein. Compositions comprising an isolated FE polypeptide or a microorganism that expresses a polypeptide of the invention are further provided. The compositions of the invention find use in methods of changing the cell wall structure of transgenic plants and therefore, making them more digestible. The method comprises introducing an FE coding sequence into the cells of a plant. Operably linked to the coding sequence is a promoter that can be either constitutive or inducible and signal sequences that serve to target expression of the coding sequence in the desired organelle in the desired cell of the plant. The signal sequences can be either or both N terminal or C terminal sequences. Optionally, a second and/or third coding sequence is introduced into the plant, such as a xylanase coding sequence, which may be co-expressed with the FE coding sequence.

"Xylanase" refers to a well described class of glycosyl hydrolases that hydrolyze xylan. Commercial applications of xylanase include the degradation and bleaching of wood pulp for paper making. Xylanase can also be added to animal feed to improve the digestibility of plant matter. Typically, commercial xylanase is derived from fungi, such as *Trichoderma*.

The FE polypeptide SEQ ID NO:3 shares homology with some previously known alpha/beta hydrolases, *Lactobacillus* esterases and cinnamoyl ester hydrolases. Members of the alpha/beta hydrolase-fold family of enzymes contain a catalytic triad of amino acids consisting of nucleophile-acid-histidine. These three amino acids are separated by a variable number of amino acid residues in the primary sequence, but are located in similar topological locations in the native protein. In most cases, the nucleophile is a serine residue. (Diaz, E., Timmis, K. N. (1995) *The Journal of Biological Chemistry* Vol. 270 No. 11, 6403-6411). Dalrymple proposed active site residues for cinI and cinII (Dalrymple, B. P. & Swadling, Y. (1997). *Microbiology* 143, 1203-1210. and Dalrymple, B. P., Swadling, Y., Cybinski, D. H. & Xue, G. P. (1996) *FEMS Microbiol Lett* 143, 115-120). BlastX analysis of ORF1 from SEQ ID NO:1 (which is set forth separately in SEQ ID NO: 2) demonstrated homology to CinII and CinI with conservation of the proposed catalytic triad (Ser, Asp and His) of Cin II and CinI within the query sequence (See GAP alignments set forth in FIGS. 1 and 2).

To determine the presence of or an increase of FE activity, an enzymatic assay can be used. These assays are readily available in the literature and those of skill in the art can readily find them. One of skill will recognize that other assays can be used to detect the presence or absence of FE. These assays include but are not limited to; immunoassays and electrophoretic detection assays (either with staining or western blotting). See, for example, Huggins and Lapides (1947) J. Biol. Chem. 170: 467-482; and Mastihuba et al. (2002) *Analytical Biochemistry* 309, 96-101.

In particular aspects, embodiments of the invention provide for methods of changing the cell wall structure of transgenic plants and therefore, making them more digestible. The method comprises introducing a ferulic acid esterase coding sequence into the cells of a plant, operably linked to a promoter that drives expression in the plant. The plant expresses the FE polypeptide, thereby causing newly conferred or increased FE expression in the plant. Expression of an FE polypeptide of the invention may be targeted to specific plant tissues where FE is particularly important, such as, for example, the leaves, stalks, or vascular tissues. Such tissue-preferred expression may be accomplished by tissue-preferred promoters, such as leaf-preferred, vascular tissue-preferred, or stalk-preferred promoters. Similarly, the timing of FE expression may be of significant importance, and accordingly, temporal promoters may be desired. For example, if expression of FE is desired after the plant has been cut, removed from the ground or ingested, an appropriate promoter would be a senescence promoter. For example, the promoter of BFN1 could be used, since BFN1 has recently been shown to be a nuclease expressed in senescing leaves, Perez-Amador, et al., (2000) *Plant Physiol.* 122:169. Similarly, the promoter of SAG12, a cysteine protease which is also found in senescing leaves, could be used (Noh & Amasino, (1999) *Plant Mol. Biol.* 41:181). Moreover, the polypeptides of the invention may also be targeted to specific subcellular locations within a plant cell.

Optionally, a second and/or third coding sequence is introduced into the plant, such as, for example, a xylanase coding sequence, which could be co-expressed with the FE coding sequence.

Just as expression of an FE polypeptide of the invention may be targeted to specific plant tissues or cell types through the use of appropriate promoters, it may also be targeted to different locations within the cell through the use of targeting information or "targeting labels." Unlike the promoter, which acts at the transcriptional level, such targeting information is part of the initial translation product. Depending on the metabolic function of the tissue or cell type, the location of the protein in different compartments of the cell may make it more efficacious or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel and Chrispeels, "Protein sorting and vesicle traffic" in Buchanan et al., eds, (2000) Biochemistry and Molecular Biology of Plants (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the polypeptide and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location.

Alternatively, the use of vacuolar targeting labels such as those described by Raikhel and Chrispeels, supra, in addition to a signal peptide will result in localization of the peptide in a vacuolar structure. As described in Raikhel and Chrispeels, supra, the vacuolar targeting label may be placed in different positions in the construct. Use of a plastid transit peptide encoding sequence instead of a signal peptide encoding sequence will result in localization of the polypeptide in the plastid of the cell type chosen (Raikhel and Chrispeels, supra). Such transit peptides are known in the art. See, for example, Von Heijne et al. (1991) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481. Chloroplast targeting sequences that encode such transit peptides are also known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6): 789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J.Biol. Chem. 268(36): 27447-27457); and the light harvesting chlorophyll a/b binding protein (LHBP) (Lamppa et al. (1988) J. Biol. Chem. 263:14996-14999). A person skilled in the art could also envision generating transgenic plants in which the chloroplasts have been transformed to over-express a gene for an FE peptide. See, for example, Daniell (1999) Nature Biotech 17:855-856; and U.S. Pat. No. 6,338,168.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have FE activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a nucleotide sequence that encodes a biologically active portion of a polypeptide of the invention will encode at least 15, 25, 30, 40, 50, 60, 70, 80, 90, 100, 110, 120, 130, 140, 150, 160, 170, 180, 190, 200, 210, 220, 230, 240, 245, 250, or 255 contiguous amino acids, or up to the total number of amino acids present in a full-length polypeptide of the invention (for example, 260 amino acids for SEQ ID NO:3). Fragments of a nucleotide sequence that are useful as hybridization probes or PCR primers generally need not encode a biologically active portion of an FE protein.

As used herein, "full-length sequence" in reference to a specified polynucleotide means having the entire nucleic acid sequence of a native sequence. "Native sequence" is intended to mean an endogenous sequence, i.e., a non-engineered sequence found in an organism's genome.

Thus, a fragment of a nucleotide sequence of the invention may encode a biologically active portion of an FE polypeptide, or it may be a fragment that can be used as a hybridization probe or PCR primer using methods disclosed below. A biologically active portion of an FE polypeptide can be prepared by isolating a portion of one of the nucleotide sequences of the invention, expressing the encoded portion of the FE protein (e.g., by recombinant expression in vitro), and assessing the activity of the encoded portion of the FE protein. Nucleic acid molecules that are fragments of a nucleotide sequence of the invention comprise at least 15, 20, 50, 75, 100, or 150 contiguous nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of one of the FE polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an FE protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 3 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, FE activity as described herein. Such variants may result from, for example, genetic polymorphism or from human manipulation. Biologically active variants of a native FE protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the FE proteins of the embodiments can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal. Such individual substitutions, deletions or additions to a polypeptide or protein sequence which alter, add or delete single amino acids or a small percentage of amino acids in the encoded sequence is a "conservatively modified variant." Such an alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired FE activity. Obviously, the mutations that will be made in the DNA encoding the variant must not place the sequence out of reading frame and optimally will not create complementary regions that could produce secondary mRNA structure. See, EP Patent No. 0075444.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that measure FE activity (See, for example, Huggins and Lapides (1947) supra, Mastihuba et al. (2002) supra.)

Variant polynucleotides and proteins also encompass sequences and proteins derived from a mutagenic and recombinogenic procedure such as DNA shuffling. With such a procedure, one or more different FE protein coding sequences can be manipulated to create a new FE protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the FE protein gene of the invention and other known FE protein genes to obtain a new gene coding for a protein with an improved property of interest, such as increased FE activity. Strategies for such DNA shuffling are known in the art. See, for example, Stemmer (1994) *Proc. Natl. Acad. Sci.* USA 91:10747-10751; Stemmer (1994) *Nature* 370:389-391; Crameri et al. (1997) *Nature Biotech.* 15:436-438; Moore et al. (1997) *J. Mol. Biol.* 272: 336-347; Zhang et al. (1997) *Proc. Natl. Acad. Sci.* USA 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other microorganisms, more particularly other bacteria. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an FE protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among FE polynucleotide sequences and are optimally at least about 10 nucleotides in length, and most optimally at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989), supra.

Similarly, the gene sequences disclosed herein, or fragments thereof, can be used as hybridization probes to screen and find other esterase producing organisms.

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) Anal. Biochem. 138: 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook, supra The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci.* USA 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, and the like.

In some embodiments, expression cassettes comprising a promoter operably linked to a heterologous nucleotide sequence of the invention that encodes an FE polypeptide are further provided. The expression cassettes of the invention find use in generating transformed plants, plant cells, and microorganisms and in practicing the methods for production of FE activity disclosed herein. The expression cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an FE polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci.* USA 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci.* USA 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci.* USA 86:5400-5404; Fuerst et al. (1989) *Proc. Natl. Acad. Sci.* USA 86:2549-2553; Deuschle et al. (1990) *Science* 248:480-483; Gossen (1993) Ph.D. Thesis, University of Heidelberg; Reines et al. (1993) *Proc. Natl. Acad. Sci.* USA 90:1917-1921; Labow et al. (1990) *Mol. Cell. Biol.* 10:3343-3356; Zambretti et al. (1992) *Proc. Natl. Acad. Sci.* USA 89:3952-3956; Baim et al. (1991) *Proc. Natl. Acad. Sci.* USA 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci.* USA 89:5547-5551; Oliva et al. (1992) *Antimicrob. Agents Chemother.* 36:913-919; Hlavka et al. (1985) Handbook of Experimental Pharmacology, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos.

5,608,149; 5,608,144; 5,604,121; 5,569,597; 5,466,785; 5,399,680; 5,268,463; 5,608,142; and 6,177,611.

In another aspect, the FE would be expressed upon ingestion by a foraging animal. Exemplary promoters for this aspect would include Soybean Gmhsp 17.5 promoter and the leucine aminopeptidase (LAP) promoter. The GMhsp promoter is from a heat shock protein gene and initiates expression if the temperature of the environment is increased. In the laboratory, an increase of 15° C. for 2 hours is the preferred heat shock. However, in non-laboratory conditions suitable increases in temperature will occur in silos and in the rumen of animals that have ingested the plants of this invention. The LAP promoter initiates the expression of the FE gene upon wounding of the plant. Such wounding would occur after cutting the plant or after mastication by a foraging animal.

Tissue-preferred expression may be accomplished by tissue-preferred promoters, such as leaf-preferred, vascular tissue-preferred, or stalk-preferred promoters. Similarly, the timing of FE expression may be of significant importance, and accordingly, temporal promoters may be desired. For example, if expression of FE is desired after the plant has been cut, removed from the ground or ingested, an appropriate promoter would be a senescence promoter. For example, the promoter of BFN1 could be used, since BFN1 has recently been shown to be a nuclease expressed in senescing leaves, Perez-Amador, et al., (2000) *Plant Physiol.* 122:169. Similarly, the promoter of SAG12, a cysteine protease which is also found in senescing leaves, could be used (Noh & Amasino, (1999) *Plant Mol. Biol.* 41:181). Moreover, the polypeptides of the invention may also be targeted to specific subcellular locations within a plant cell.

Additionally, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing Rcg1 with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792, 931); avirulence and disease resistance genes (Jones et al. (1994) *Science* 266:789; Martin et al. (1993) Science 262: 1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The methods of the invention involve introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the invention do not depend on a particular method for introducing a sequence into a plant, only that the polynucleotide gains access to the interior of at least one cell of the plant. Methods for introducing polynucleotides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include, but are not limited to, microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055- and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the FE sequences of the invention can be provided to a plant using a variety of transient transformation methods. Such transient transformation methods include, but are not limited to, the introduction of the FE protein or variants and fragments thereof directly into the plant or the introduction of the FE protein transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the an FE polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant that has stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5; etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., increased digestibility), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" by Fehr, (1993) Macmillan Publishing Company, the disclosure of which is incorporated herein by reference. In addition, mutations created in other lines may be used to produce a backcross conversion of elite lines that comprises such mutations.

As used herein, the term plant includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

As mentioned above, the transgenic plants of this invention can be used as feed or for silage production for animals, such as cattle, sheep, goats, horses, pigs, poultry, and other livestock. In addition, the methods of this invention can be used to transform any plant into which FE expression is desired. For example, it is advantageous to break down cell walls during biomass conversion or during processing of plants for foodstuffs. This invention would help to achieve this goal more effectively and inexpensively.

The inventive methods herein may also be used to provide enzymes to enhance the availability of fermentable sugars in plants, through polypeptide addition to plant material or via fermentation with recombinant bacteria containing the polynucleotides. Carbohydrates may be subject to further modification, either exogenously or endogenously, by the action of other enzymes. Such enzymes include, but are not limited to, endoglucanases, xylosidases and/or cell biohydrolases. These enzymes may be provided either in an expression cassette provided for herein (i.e., endogenous) or applied to the plant cell walls (i.e., exogenous) to enhance the availability of mono- and/or di-saccharides.

Plants other than grasses may find a use in the present invention. For example, corn (or maize) is contemplated to be useful. The grass *Festuca* is similar to maize in cell wall structure and therefore provides a good model of the ability to enhance the availability of fermentable carbohydrates in corn. Other useful plants contemplated for use in the present invention include, but are not limited to, *Festuca, Lolium, Zea, Avena, Sorghum, Millet* (tropical cereals), *Miscanthus* (a grass with potential for use as a biomass energy crop), *Cenchrus, Dichanthium, Brachiaria* and *Paspalum* (apomictic tropical range grasses) and *Poa* (Kentucky bluegrass).

A gene encoding an FE polypeptide of the invention may be introduced into any suitable microbial host according to standard methods in the art. For example, microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, and to provide for stable maintenance and expression of the gene expressing the protein.

Genes encoding FE polypeptides of the invention, or fragments thereof, can also be used to transform bacteria with the intention of using the transformed bacteria as a silage inoculant, probiotic, food starter culture or for use in the production of food or feed additives by fermentation. Organisms that would be useful in such situations include, but are not limited to, *Lactobacillus, Lactococcus, Enterococcus, Pediococcus* and *Leuconostoc*. Likewise, the genes encoding the FE polypeptides of the invention, or fragments thereof, can be used to transform bacteria for the purposes of biofuel production (See Tabka, M. G. et al. (2006) *Enzyme and Microbial Technology* 39: 897-902.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Pediococcus, Enterococcus, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Other organisms of interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Also of interest are the pigmented microorganisms.

Other illustrative prokaryotes, both Gram-negative and gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The article "a" and "an" are used herein to refer to one or more than one (i.e., to at least one) of the grammatical object of the article. By way of example, "an element" means one or more elements.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The following examples are provided by way of illustration, not by way of limitation.

EXPERIMENTAL

Example 1

Ferulate Esterase Gene Cloning

Total DNA from *Lactobacillus buchneri* strain LN4017, deposited as Patent Deposit No. PTA-6138, was used to generate an *E. coli* clone which expressed FE activity. Size-fractionated partial Sau3AI digested total DNA libraries of LN4017 were constructed. Approximately 1000 clones were screened for FE activity in *E. coli* DH5alpha by looking for zones of clearing on Difco™ Luria-Bertani agar plates containing 50 µg/mL Ampicillin, 80 µM IPTG and 0.12% ethyl 4-hydroxy-3-methoxycinnamate. One FE positive clone was identified and found to contain a 3 kb insert in pUC18. The plasmid DNA was transformed into *E. coli* Novablue cells and a number of transformants were generated including clone EF-1. This clone also showed zones of clearing on agar plates.

The 3 kb EF-1 clone was cut into smaller fragments with convenient restriction enzymes and sub-cloned into pUC18, using DH5alpha as the cloning host. Removal of a 0.45 kb fragment from one end generated sub-clone A which retained activity on agar plates. The remaining two fragments were used to generate sub-clone B, which was 1.4 kb in length and sub-clone C, which was 1.2 kb in length (see FIG. 3). Background esterase activity (or possibly pH drop) from the *E. coli* host made it difficult to determine whether sub-clones B and C had activity on agar plates.

Example 2

Ferulate Esterase Gene Sequence Analysis

DNA sequencing was conducted on clone EF-1 and on sub-clones A, B and C. Sequence analysis of an ORF (SEQ ID NO: 2) from sub-clone B indicated that it encoded a peptide (SEQ ID NO: 3) of 260 amino acids with a 28 kDa molecular weight. BLASTX analysis of SEQ ID NO: 2 detected a number of amino acid homologies including homology to alpha/beta hydrolases (including Accession Nos: AAK81587, AAM25001), *Lactobacillus* esterases (including Accession Nos: AAV43644, CAD65143) and cinnamoyl ester hydrolases (including Accession No: ZP_00732443). Esterase active site residues appeared to be conserved.

Sub-clone C was resistant to sequencing on one end, possibly due to secondary structure within the DNA. Multiple primers from both directions were attempted. The region was ultimately sequenced using DNA from the 3 kb clone EF-1 and sub-clone A and the resulting ORF is set forth herein as SEQ ID NO: 4, which encodes SEQ ID NO: 5. BlastX analysis of SEQ ID NO: 4 generated hits to acetyl esterases, including one from *L. plantarum* (Accession No: CAD64912). There was some homology detected to a *Neurospora crassa* feruloyl esterase B precursor (Accession No: CAC05587).

The peptide encoded by ORF1 is set forth in SEQ ID NOs: 3 and has been shown to be a member of the alpha/beta hydrolase-fold family of enzymes, which contain a catalytic triad of amino acids consisting of nucleophile-acid-histidine. These three amino acids are separated by a variable number of amino acid residues in the primary sequence, but are located in similar topological locations in the native protein. In most cases, the nucleophile is a serine residue. (Diaz, E., Timmis, K. N. (1995) *The Journal of Biological Chemistry* Vol. 270 No. 11, 6403-6411). GAP alignments of the peptide of SEQ ID NO: 3 with other hydrolases demonstrated conservation of the catalytic triad (Ser, Asp and His). (See FIGS. 1 and 2) In addition, the peptide showed the conserved pentapeptide sometimes referred to as the nucleophile elbow. This pentapeptide motif is characterized by a glycine followed by any amino acid, followed by a serine, followed by any amino acid, followed by another glycine (Schrag, J. D. and Cygler, M. (1997) *Methods in Enzymology* Vol 284: 85-107).

Sub-clone C does not appear to contain the complete open reading frame; the first few amino acids appear to be encoded by the end of sub-clone B (see FIG. 3). The putative ORF of 266 amino acids encodes a 28 kDa protein.

Example 3

Ferulate Esterase and Acetyl Esterase Activity Assays

The FE and AE activities of the 3 kb clone, EF-1 (discussed in Example 1), and of sub-clones A, B and C, were assayed according to the protocols described below. As shown in Table 1, cell lysates from clone EF-1 (which contains the ORFs for the peptides of SEQ ID NOs: 3 and 5) and sub-clone A (which is missing an upstream non-coding region) had strong FE and AE activity. Sub-clone B (which contains the ORF for the peptide of SEQ ID NO: 3) had FE activity but lacked AE activity, relative to the vector-only control. Sub-clone C (which encodes a smaller portion of the peptide of SEQ ID NO: 5) had neither AE activity nor FE activity, relative to the vector-only control. This data suggests that the peptide of SEQ ID NO: 3 is an FE enzyme, while the peptide of SEQ ID NO: 5 is an AE enzyme.

TABLE 1

Activity Levels of Cleared Lysates. Activity is expressed as nmoles pNP released/min/mg protein.

| Sample | Details[1] | FE[2] | AE[3] |
|---|---|---|---|
| pUC18 | vector only | 0.11 | 0.72 |
| Clone EF-1 | entire insert | 3.39 | 3.70 |
| subclone A | Subclone - missing part of upstream non-coding region | 3.13 | 3.38 |
| subclone B | Subclone - contains Est1 | 1.05 | 0.72 |
| subclone C | Subclone - contains part of Est2 | 0.11 | 0.60 |

[1]*E. coli* host strain DH5alpha was used for all recombinants
[2]FE, Ferulic Acid Esterase
[3]AE, Acetyl Esterase Determination of Acetyl or Ferulate Esterase Activity Lactic acid bacterial cultures were grown in De Man Rogosa Sharpe broth (MRS broth; Difco™ Lactobacilli MRS; Becton Dickinson and Company, Sparks, Md. 21152 USA), prepared as described by the manufacturer, for 24 to 48 hours. *E. coli* cultures were grown with aeration in Difco™ Luria-Bertani broth containing 50 µg/mL ampicillin for 16-17 hours. The bacterial cells were harvested by centrifugation (18000×g; 5 min) and resuspended in PBS, Phosphate Buffered Saline, containing sodium azide (10 µg/mL). Cells were lysed using a French Press (Thermo Spectronic Instruments, Inc., Rochester, N.Y.) as is known in the art. Cleared lysates were obtained by centrifugation at 18000×g for 10 min. Test samples (cleared lysates or soluble protein) were then assayed for acetyl or ferulate esterase activity using methods described previously (Huggins and Lapides (1947) J. Biol. Chem. 170: 467-482; Mastihuba et al. (2002) *Analytical Biochemistry* 309, 96-101) with modifications as detailed below.

The substrates for AE activity, 4-nitrophenyl acetate (4NPAc, Sigma-Aldrich, St. Louis, Mo.); and FE activity, 4-nitrophenyl ferulate (4NPF, Institute of Chemistry, Slovak Academy of Sciences Dubravska, Cesta 9, 845 38, Slovakia) were dissolved in dimethyl sulphoxide (DMSO) and diluted 10-fold to the final working substrate solution of 2.5 mM in 0.5 M potassium phosphate containing 2.5% Triton X-100 (pH6.0 for 4NPAc, pH7.0 for 4NPF). Using microtiter plates, reaction mixtures contained 80 µL of substrate and 20 µL of test sample and were incubated at 37° C. for 60 min. Control wells consisting of 1) 4NPAc or 4NPF substrate solution and 2) test samples were included and otherwise treated the same way as the reaction mixtures. Following the incubation period, each reaction was diluted 10-fold in 0.5 M potassium phosphate containing 10% DMSO (pH 8.0) and the optical density was determined at 405 nm (SpectraMax 190 Microplate Reader, Molecular Devices, Menlo Park Calif.). Reaction mixture absorbance readings were corrected for absorbance readings of controls. Concentration of p-nitrophenol was determined by reference to a standard curve. Protein concentrations were determined according to the method published by Bradford (Bradford, M, (1976) Analytical Biochemistry 72 248-254). AE or FE activities of the samples were expressed as nmoles of p-nitrophenol (pNP) released per minute per mg of protein.

Example 4

Ferulate Esterase Gene Protein Expression

In order to express the LN4017 esterase genes in *E. coli*, the ORF set forth in SEQ ID NO: 2 and 4 were PCR cloned in the Invitrogen Gateway® cloning vector pDONR221. Two Gateway® clones, pENTR221-Est1 and pENTR221-Est 2, recombined into the Gateway® vector pET28-His 7. The Est 1 and Est 2 proteins (SEQ ID NO: 3 and 5, respectively) were expressed with histidine fusion tags in *E. coli* strain BL21 (DE3) Gold and purified using standard protocols for column elutions. Soluble protein elution fractions were used to run enzyme assays as described in Example 3 and were compared to cleared cell lysate from *L. buchneri* LN4017. As shown in Table 2, although both elution proteins display both FE and AE activity, the Est 1 protein displays a much stronger FE activity, while Est 2 displays stronger AE activity. This is consistent with the results of Example 3 and the Blast X analysis of the ORFs. The weaker activities were not detected until the ORFs were placed into the T7 expression vector.

TABLE 2

FE and AE Activity of Purified Proteins. Activity is expressed as nmoles pNP released/min/mg protein

| Sample | FE[1] | AE[2] |
|---|---|---|
| LN4017 | 10.47 | 14.09 |
| HisT7-Est1 (SEQ ID NO: 3) | 142.04 | 13.14 |
| HisT7-Est2 (SEQ ID NO: 5) | 43.70 | 66.72 |

[1]FE, Ferulic Acid Esterase
[2]AE, Acetyl Esterase

Example 5

Transformation and Regeneration of Transgenic Maize Plants

Immature maize embryos from greenhouse donor plants are bombarded with a plasmid containing a nucleotide sequence encoding the FE polypeptide set forth in SEQ ID NO:1 operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

Preparation of DNA

A plasmid vector comprising a nucleotide sequence encoding the FE polypeptide set forth in SEQ ID NO:3 operably linked to a promoter that drives expression in a maize cell is made. This plasmid DNA plus plasmid DNA containing a selectable marker (e.g., PAT) is precipitated onto 1.1 μm (average diameter) tungsten pellets using a $CaCl_2$ precipitation procedure as follows:

100 μL prepared tungsten particles in water
  10 μL (1 μg) DNA in Tris EDTA buffer (1 μg total DNA)
  100 μL 2.5 M $CaCl_2$
  10 μL 0.1 M spermidine Each reagent is added sequentially to the tungsten particle suspension, while maintained on the multi-tube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for fungal resistance.

Bombardment and Culture Media

Bombardment medium (560Y) comprises 4.0 g/L N6 basal salts (SIGMA C-1416), 1.0 mL/L Eriksson's Vitamin Mix (1000×SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 6

Agrobacterium-Mediated Transformation of Maize and Regeneration of Transgenic Plants For *Agrobacterium*-mediated transformation of maize with a nucleotide sequence encoding the polypeptide of SEQ ID NO:3, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the polynucleotide construct to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A DNA construct comprising a promoter that drives expression in a plant or plant cell operably linked to a nucleotide sequence, wherein the nucleotide sequence is selected from the group consisting of:
   a) a polynucleotide comprising SEQ ID NO: 2;
   b) a polynucleotide having at least about 95% sequence identity to SEQ ID NO: 2, wherein said polynucleotide encodes a polypeptide having ferulate esterase activity;
   c) a polynucleotide encoding SEQ ID NO: 3; and
   d) a polynucleotide encoding a polypeptide having at least 95% sequence identity to SEQ ID NO: 3 wherein said polypeptide has ferulate esterase activity .

2. The DNA construct of claim 1, wherein the nucleotide sequence is derived from a *Lactobacillus* species.

3. The DNA construct of claim 2, wherein the *Lactobacillus* species is *Lactobacillus buchneri*.

4. The DNA construct of claim 1 further comprising an operably linked polynucleotide encoding a signal peptide.

5. The DNA construct of claim 1, wherein the DNA construct further comprises a polynucleotide sequence that targets expression of the polynucleotide.

6. A transformed plant cell comprising at least one DNA construct according to claim 1.

7. The plant cell of claim 6, wherein said plant cell is from a monocot.

8. The plant cell of claim 7, wherein said monocot is a member of a genus selected from the group consisting of *Festuca*, *Lolium*, *Sorghum*, *Zea*, *Triticum*, *Avena*, and *Poa*.

9. A transgenic plant comprising at least one DNA construct according to claim 1.

10. The transgenic plant of claim 9, wherein said plant displays increased digestibility.

11. The transgenic plant of claim 9, wherein the nucleotide sequence is derived from a *Lactobacillus* species.

12. The transgenic plant of claim 11, wherein the *Lactobacillus* species is *Lactobacillus buchneri*.

13. The transgenic plant of claim 9 wherein the promoter is selected from the group consisting of:
   a) an inducible promoter;
   b) a senescence promoter;
   c) an embryo specific promoter;
   d) a pericarp specific promoter;
   e) a heat shock promoter; and
   f) a constitutive promoter.

14. The transgenic plant of claim 9, wherein said plant is a monocot.

15. The transgenic plant of claim 14, wherein said monocot is a member of a genus selected from the group consisting of *Festuca*, *Lolium*, *Sorghum*, *Zea*, *Triticum*, *Avena*, and *Poa*.

16. A transformed seed of the transgenic plant of claim 9, wherein the seed comprises the construct.

17. The transgenic plant of claim 9, further comprising introduction into the plant a second DNA construct comprising a promoter operably linked to a xylanase encoding polynucleotide.

18. The transgenic plant of claim 17, wherein the first and second DNA constructs are present on separate plasmids.

19. A method of affecting the cross-linking of phenolic acids in plant cell walls of a transgenic plant, the method comprising introducing into the plant a DNA construct comprising a promoter operably linked to an isolated polynucleotide, wherein said polynucleotide has a sequence selected from the group consisting of:
   a) a polynucleotide comprising SEQ ID NO: 2;
   b) a polynucleotide having at least about 95% sequence identity to SEQ ID NO: 2; wherein said polynucleotide encodes a polypeptide having ferulate esterase activity
   c) a polynucleotide encoding SEQ ID NO: 3; and
   d) a polynucleotide encoding a polypeptide having at least 95% sequence identity to SEQ ID NO: 3 wherein said polypeptide has ferulate esterase activity.

20. The method of claim 19, wherein the polynucleotide is derived from a *Lactobacillus* species.

21. The method of claim 20, wherein the *Lactobacillus* species is *Lactobacillus buchneri*.

22. The method of claim 19, wherein said plant is a monocot.

23. The method of claim 22, wherein said monocot is a member of a genus selected from the group consisting of *Festuca*, *Lolium*, *Sorghum*, *Zea*, *Triticum*, *Avena*, and *Poa*.

24. The method of claim 19, further comprising introduction into the plant a second DNA construct comprising a promoter operably linked to a xylanase encoding polynucleotide.

25. The method of claim 24, wherein the first and second DNA constructs are present on separate plasmids.

26. A transgenic plant produced by the method of claim 19.

27. A method for increasing digestibility of a plant or plant part fed to an animal, the method comprising introducing into a plant a DNA construct comprising a promoter operably linked to a polynucleotide, wherein said polynucleotide has a sequence selected from the group consisting of:
   a) a polynucleotide comprising SEQ ID NO: 2;
   b) a polynucleotide having at least about 95% sequence identity to SEQ ID NO: 2, wherein said polynucleotide encodes a polypeptide having ferulate esterase activity;
   c) a polynucleotide encoding SEQ ID NO: 3; and
   d) a polynucleotide encoding a polypeptide having at least 95% sequence identity to SEQ ID NO: 3 wherein said polypeptide has ferulate esterase activity.

28. The method of claim 27, wherein the polynucleotide is derived from *Lactobacillus buchneri*.

29. The method of claim 27, wherein said plant is a monocot.

30. The method of claim 29, wherein said monocot is a member of a genus selected from the group consisting of *Festuca*, *Lolium*, *Sorghum*, *Zea*, *Triticum*, *Avena*, and *Poa*.

31. The method of claim 27, further comprising introduction into the plant a second DNA construct comprising a promoter operably linked to a xylanase encoding polynucleotide.

32. The method of claim 31, wherein the first and second DNA constructs are present on separate plasmids.

33. A transgenic plant produced by the method of claim 27.

34. An isolated nucleic acid molecule comprising a nucleotide sequence selected from the group consisting of:
   a) a polynucleotide comprising SEQ ID NO: 2;
   b) a polynucleotide having at least about 95% sequence identity to SEQ ID NO 2, wherein said polynucleotide encodes a polypeptide having ferulate esterase activity;
   c) a polynucleotide encoding SEQ ID NO: 3; and
   d) a polynucleotide encoding polypeptide having at least 95% sequence identity to SEQ ID NO: 3, wherein said polypeptide has erulate esterase activity.

35. The nucleic acid molecule of claim 34, wherein said nucleotide sequence is optimized for expression in a plant.

* * * * *